United States Patent
Sohn et al.

(10) Patent No.: US 6,333,422 B1
(45) Date of Patent: Dec. 25, 2001

(54) THERMOSENSITIVE CYCLOTRIPHOSPHAZENE-PLATINUM COMPLEX CONJUGATE, ITS PREPARATION METHOD AND ANTICANCER AGENT CONTAINING THE SAME

(75) Inventors: Youn Soo Sohn; Soo-Chang Song; Sang Beom Lee, all of Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/771,716

(22) Filed: Jan. 30, 2001

(30) Foreign Application Priority Data

Aug. 21, 2000 (KR) .................................................. 12-48360

(51) Int. Cl.$^7$ .................................. C07F 9/06; C07F 9/65
(52) U.S. Cl. .............................. 556/17; 556/13; 514/110; 514/492
(58) Field of Search ........................ 556/13, 17; 514/110, 514/492

(56) References Cited

U.S. PATENT DOCUMENTS

| | | |
|---|---|---|
| 4,151,185 | 4/1979 | Allcock et al. . |
| 5,104,947 | 4/1992 | Schacht et al. . |
| 5,665,343 | 9/1997 | Sohn et al. . |
| 6,133,387 * | 10/2000 | Xu et al. .............. 556/13 X |
| 6,221,906 | 4/2001 | Sohn et al. . |
| 6,239,061 * | 5/2001 | Wang et al. ............ 556/13 X |

FOREIGN PATENT DOCUMENTS

| | | |
|---|---|---|
| 2 284 197 | 9/1988 | (EP) . |
| 0 290 280 | 11/1988 | (EP) . |
| 98-0023695 | 6/1998 | (KR) . |
| 98-0164460 | 9/1998 | (KR) . |
| 99-0010532 | 3/1999 | (KR) . |
| 48800/1999 | 11/1999 | (KR) . |
| 81/00256 | 2/1981 | (WO) . |

OTHER PUBLICATIONS

Sang Beom Lee et al., "Thermosensitive Cyclotriphosphazenes", Jrnl. of the Amer. Chem. Soc., vol. 122, No. 34, pp. 8315–8316, 2000.

Lee, S.B. et al., "A new class of biodegradable thermosensitive polymers. 2. Hydrolytic properties and salt effect on the lower critical solution temperature of poly(organophosphazenes) with methoxypoly(ethylene glycol) and amino acid esters as side groups", Macromolecules, 32, 7820. (1999).

S. Song et al., "A new class of biodegradable thermosensitive polymers. I. Synthesis and characterization of poly(organophosphazenes) with methoxy–poly(ethylene glycol) and amino acid esters as side groups . . . ", Macromolecules, v. 32, No. 7, pp. 2188–2193 (1999).

B. Jeong, "Biodegradable block copolymers as injectable drug–delivery systems", Nature, v. 388, p. 860–862 (Aug. 1997).

M. J. Cleare, "Anti–tumour platinum complexes: relationships between chemical properties and activity", Biochimie, 60, 835 (1978).

\* cited by examiner

*Primary Examiner*—Paul F. Shaver
(74) *Attorney, Agent, or Firm*—Morrison & Foerster LLP

(57) ABSTRACT

The present invention provides a novel thermosensitive cyclotriphosphazene-platinum complex conjugates represented by Formula 1, Formula 1

$$\mathrm{-(N{=}P)_3{-}} \begin{array}{l} \mathrm{O{-}(CH_2CH_2O)_m{-}(CH_2)_nCH_3} \\ \mathrm{HN{-}CHCOO} \\ \quad \quad \quad \quad \quad \diagdown \mathrm{PtA_2} \\ \mathrm{(CH_2)_xCOO} \diagup \end{array}$$

wherein m is a repeating unit of poly(alkoxyethylene glycol) selected from the integers 2, 7 and 12; n represents the length of the alkyl chain selected from the integers 0, 1, 2 and 3; x represents the length of the anionic amino acid residue selected from the integers 0 (amino malonic acid derivatives), 1 (aspartic acid derivatives) and 2 (glutamic acid derivatives); $A_2$ is a bidentate chelating diamine selected from the group consisting of 2,2-dimethyl-1,3-propanediamine (dmpda), trans(±)-1,2-diaminocyclohexane (dach) and 1,1-diaminomethylcyclohexane (dmach).

15 Claims, No Drawings

THERMOSENSITIVE CYCLOTRIPHOSPHAZENE-PLATINUM COMPLEX CONJUGATE, ITS PREPARATION METHOD AND ANTICANCER AGENT CONTAINING THE SAME

BACKGROUND OF THE INVENTION

The present invention relates to a thermosensitive cyclotriphosphazene-platinum complex conjugate which can be administered systemically or locally and has an excellent anticancer activity, its preparation method and an anticancer agent containing the same as an active ingredient. More particularly, the compound of the present invention is a biodegradable cyclotriphosphazene-platinum complex conjugate exhibiting thermosensitivity in the temperature range including the body temperature.

The present inventors have found that the derivatives obtained by nucleophilic substitution of chlorine atoms in hexachlorocyclotriphosphazene ($(NPCl_2)_3$) with a low or high molecular weight hydrophilic poly(alkoxyethylene glycol) and a hydrophobic amino acid ester exhibit thermosensitivity (Korean patent application No. 99-48800). The present inventors have succeeded in the preparation of their platinum complexes by introducing the (diamine)platinum(II) ion to the hydrolyzed amino acid groups of these trimeric derivatives. To our surprise, these novel trimeric platinum complex conjugates also exhibited thermosensitivity in a wide temperature range including the body temperature as well as high anticancer activity. These new thermosensitive platinum complex conjugate anticancer agents showing a controlled release property has never been reported. These compounds can be administered systemically or locally since the targeted drug delivery is possible using their thermosensitivity. We expect, therefore, these new compounds will provide a new and significantly improved therapeutic regimen in the treatment of solid tumors.

Thermosensitive polymers in the present invention refer to the polymers that can be solubilized in water at low temperatures but precipitates above a certain critical temperature due to the rapid decrease of their water-solubility. When such a phase transition is reversible, the phase transition temperature is called a lower critical solution temperature(LCST) or a cloud point. Below LCST, the hydrogen bonding between the polymer-water molecules is stronger than the hydrophobic interaction between the polymer-polymer molecules. As the temperature increases, however, the hydrogen bonding between the polymer-water molecules weakens whereas the hydrophobic interaction between the polymer-polymer molecules increases resulting in the precipitation of polymers in aqueous solution.

These thermosensitive polymers were widely studied in many fields is including mainly drug delivery systems, medical biomaterials, thin films, the separation process of biochemical reactions, cosmetics and optics. However, most of the conventional thermosensitive organic polymers are known to be hydrolytically non-degradable. In recent years, a few biodegradable polymers were reported (Jeong, B. et. al., *Nature*, 388, 860 (1997); Song, S.-C. et. al., *Macromolecules*, 32, 2188(1999); Lee, S. B. et. al., *Macromolecules*, 32, 7820 (1999)). Up to date, however, no thermosensitive anticancer drug has been reported. Cisplatin, a platinum complex, approved as an anticancer agent in 1979 by FDA in the United States has been used as one of the most effective chemotherapeutic agents to treat a variety of cancers such as testicular, ovarian, bladder, and head and neck cancers. Its use is limited, however, due to its high toxicity ($LD_{50}$=13 mg/Kg, M. J. Cleare, Biochimie 60, 835(1978)). Even though the second-generation anticancer agent, carboplatin exhibits much lower toxicity than cisplatin ($LD_{50}$=180 mg/Kg, M. J. Cleare, Biochimie 60, 835 (1978)), it is not widely used since it is lower in anticancer activity and more expensive than cisplatin. Therefore, there is a great need for a third-generation anticancer agent that has higher and wider anticancer activity with lower toxicity than cisplatin.

SUMMARY OF THE INVENTION

Therefore, an object of the present invention is to develop a third-generation anticancer agent having a higher anticancer activity and lower toxicity than the conventionally used cisplatin.

To achieve this goal, the present inventors have discovered a novel class of the cyclotriphosphazene-platinum complex conjugate anticancer agents whose LCST can be designed variably for the desired purpose and controlled precisely, by introducing the solubilizing agent and the platinum complex into the biodegradable cyclotriphosphazene. These new cyclotriphosphazene-platinum complex conjugate anticancer agents of the present invention may be administered systemically or locally by using the thermosensitive properties of the drugs.

More particularly, an object of the present invention is to provide oligomeric thermosensitive cyclotriphosphazene-platinum complex conjugates having a stereo-specific chemical structure and LCST that can be designed for the desired purpose, by nucleophilic substitution of the chlorine atoms in hexachlorocyclotriphosphazene with a poly (alkoxyethylene glycol) and an amino acid ester, followed by hydrolysis of the substituted amino acid ester and subsequent reaction with a (diamine)platinum salt and the preparation method thereof.

Another object of the present invention is to provide an anticancer agent having the thermosensitive cyclotriphosphazene-platinum complex conjugate as an active ingredient.

DETAILED DESCRIPTION OF THE INVENTION

To achieve the above-mentioned goals, the present inventors have performed the following experiments. Hexachlorocyclotriphosphazene was reacted first with a hydrophilic poly(alkoxyethylene glycol) having different molecular weights, and then with a variety of hydrophobic amino acid esters to obtain a new class of cyclotriphosphazene derivatives with thermosensitive properties. The substituted amino acid eaters in the trimers were hydrolyzed with alkali, and then reacted with a (diamine)platinum(II) salt to obtain a cyclotriphosphazene-platinum complex conjugate formed by covalent bonding between the carboxylate groups of the amino acid and the platinum(II) cation. Surprisingly, we have found that these trimeric platinum conjugates exhibit thermosensitivity in a wide range of temperature depending on the kinds of substituents and the platinum derivatives. Furthermore, we have found that the LCST of the cyclotriphosphazene-platinum complex conjugates can be designed and controlled for the desired application purpose since the LCST of these cyclotriphosphazene-platinum complex can be varied easily by appropriate choice of different poly(alkoxyethylene glycol), amino acid and platinum derivatives.

The preparation method of the novel stereo-specific cyclotriphosphazene-platinum complex conjugates represented by Formula 1 of the present invention is described in detail as follows.

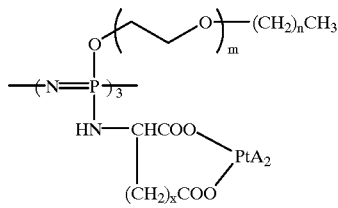

Formula 1 wherein, m is an integer selected from 2, 7 and 12; n is an integer selected from 0, 1, 2 and 3; x is an integer selected from 0, 1 and 2; and $A_2$ is a bidentate chelating diamine selected from the group consisting of 2,2-dimethyl-1,3-propanediamine (dmpda), trans($\pm$)-1,2-diaminocyclohexane (dach) and 1,1-diaminomethylcyclohexane (dmach).

In the above, m selected from the integer of 2, 7, or 12 is a repeating unit of poly(alkoxyethylene glycol), n selected from the integer of 0 to 3 represents the length of the alkyl chain, x selected from the integer of 0 to 2 represents the length of the anionic amino acid residue.

The trimeric amino acid ester derivatives represented by Formula 2 was prepared by reacting hexachlorocyclotriphosphazene first with hydrophilic poly(alkoxyethylene glycol) and then with a variety of hydrophobic amino acid esters. By reacting the trimeric derivatives of Formula 2 with 3 moles of alkali earth metal hydroxide of Formula 3 or with 6 moles of alkali metal hydroxide of Formula 4 in methanol or ethanol for 3~5 hours, the intermediate cyclotriphosphazene-alkali earth metal salt of Formula 5 or the cyclotriphosphazene-alkali metal salt of Formula 6, respectively, were obtained. With this intermediate, 3 moles of (diamine)platinum sulfate or nitrate of Formula 7 was reacted in distilled water for 3~7 hours at 1~5° C., and then the reaction mixture was freeze-dried.

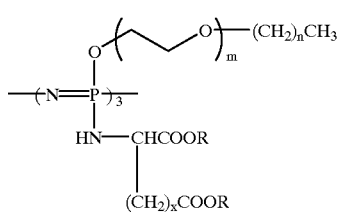

Formula 2

M(OH)$_2$      Formula 3

M'OH           Formula 4

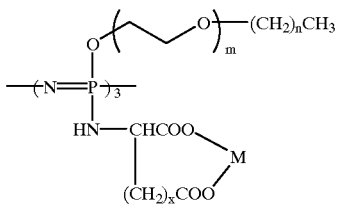

Formula 5

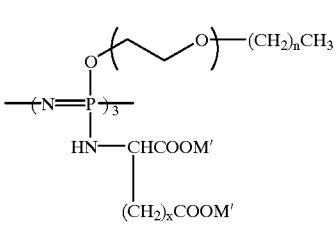

Formula 6

$A_2PtL_2$     Formula 7

In Formulas 2–7, m, n, x and A are as defined as in Formula 1; R is selected from the group consisting of methyl, ethyl or benzyl groups; M is an alkali earth metal ion such as barium or calcium; M' is an alkali metal ion such as lithium, sodium or potassium; and $L_2$ is selected from sulfate or nitrate ion.

The aqueous solution of (diamine)platinum salt of Formula 7 was prepared by reacting (diamine)platinum iodide with an acidic salt of silver according to the method in the literature (R. C. Harrison, Inorg. Chimica Acta 46, L15 (1980)).

To the above freeze-dried product was added alcohol with stirring and then the solution mixture was centrifuged. After the supernatant solution was separated and condensed by evaporation at a reduced pressure, an excess amount of ether or hexane was added to precipitate the final product. The precipitation process using a solvent pair of alcohol/ether or hexane was repeated 2~3 times and the final precipitate was vacuum-dried. To remove small amounts of other isomers in the final product, an appropriate LCST lowering compound (NaCl, KCl, $CF_3CH_2OH$, or $CH_3(CH_2)_3OH$) depending on the LCST of the isomeric forms of the trimeric derivatives was added to the aqueous solution of the product to induce precipitation of the purer product. The supernatant aqueous phase was removed by centrifugation to obtain the purified precipitate. This purification process was repeated 2~3 times and then the final solution was freeze-dried to obtain the thermosensitive cyclotriphosphazene-platinum complex conjugates of Formula 1.

The preparation process of the present invention is schematically represented in the following Reaction Scheme 1.

Reaction Scheme 1

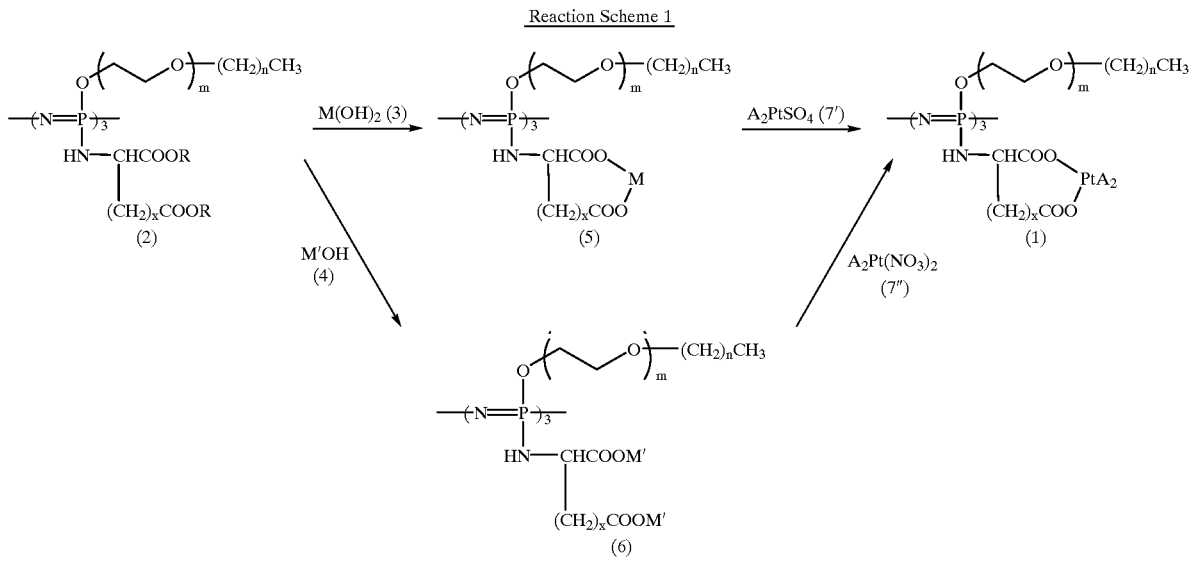

The invention will be further illustrated by the following examples, but is not limited to the examples given.

Elemental analysis of carbon, hydrogen, nitrogen in the compounds of the present invention was performed in the Special Analysis Center at KIST by using carbon, hydrogen and nitrogen analyzer (Perkin Elmer), and phosphorous and platinum analysis was performed using Polyscan 61E ICP. Hydrogen and phosphorous nuclear magnetic resonance spectra were obtained using Varian to Gemini-300, and LCST was measured by using Perkin-Elmer Lamda 18 UV/VIS spectrophotometer.

EXAMPLES

Example 1

Preparation of $\{NP[(OCH_2CH_2)_2OCH_3][L\text{-}Asp.Pt(dmpda)]\}_3$

After dissolving $\{NP[(OCH_2CH_2)_2OCH_3][NHCH(CH_2COOC_2H_5)COOC_2H_5]\}_3$ (1.00 g, 0.95 mmol) in methanol(50ml), the temperature of the reaction vessel was controlled to 0~5° C. by using ice-water bath. To this solution was slowly added with stirring a methanol solution containing an excess amount of $Ba(OH)_2 \cdot 8H_2O$(1.19 g, 3.78 mmol). After 30 min. the ice-water bath was removed and then the reaction was continued further for 3 hours. The reaction mixture was concentrated at reduced pressure until only a small amount of solvent remained. An excess amount of ether or hexane was added to the concentrated reaction mixture to induce precipitation of the hydrolysis product. The precipitate thus obtained was re-dissolved in a small amount of methanol and re-precipitated by adding an excess amount of ether or hexane. After repeating the precipitation process 2–3 times, the final precipitate was dried in vacuum to obtain 0.99 g of cyclotriphosphazene-barium salt (yield, 93%). This trimeric barium salt (0.99 g, 0.87 mmol) was dissolved in 20 ml of distilled water and the temperature of the reaction vessel was controlled to 1~5° C. by using ice-water bath. To this solution was added drop-wise in 30 min. an aqueous solution prepared by dissolving (dmpda)PtSO$_4$ (0.87 g, 2.62 mmol) in distilled water. The reaction mixture was reacted for 3 hours and then freeze-dried. An excess amount of methanol or ethanol was added to the dried mixture and stirred to extract the cyclophosphazene-platinum complex conjugate. To increase the purity of the final conjugate product, the purification process comprising dissolution of the conjugate product in a small amount of methanol or ethanol and precipitation by adding an excess amount of ether or hexane has been repeated 2~3 times. The final precipitate was dried in vacuum to obtain the final product (1.25 g, yield, 81.0%).

Molecular formula: $C_{42}H_{87}N_{12}O_{21}P_3Pt_3$

Elemental analysis (%): C, 27.59; H, 4.80; N, 9.55; P, 5.15; Pt, 31.56

Theoretical value: C, 28.43; H, 4.94; N, 9.47; P, 5.24; Pt, 32.98

Proton nuclear magnetic resonance spectrum (D$_2$O, ppm):

δ0.9–1.2 (b, 6H, H$_2$NCH$_2$C(C$\underline{H}_3$)$_2$CH$_2$NH$_2$),

δ2.3–2.7 (b, 6H, H$_2$NC$\underline{H}_2$C(CH$_3$)$_2$C$\underline{H}_2$NH$_2$, —NHCH(C$\underline{H}_2$COO)COO), δ3.4 (s, 3H, —O(CH$_2$CH$_2$O)$_2$C$\underline{H}_3$), δ3.6–3.9 (b, 6H, —OC$\underline{H}_2$C$\underline{H}_2$OC$\underline{H}_2$C$\underline{H}_2$OCH$_3$), δ4.1–4.4 (b, 3H, —OCH$_2$CH$_2$CH$_2$OCH$_2$CH$_2$OCH$_3$, —NHC$\underline{H}$(CH$_2$COO)COO), Phosphorus nuclear magnetic resonance spectrum (D$_2$O, ppm): δ32–48

Lower critical solution temperatures: 98.0° C.

Example 2

Preparation of $\{NP[(OCH_2CH_2)_2OCH_3][L\text{-}Asp.Pt(dach)]\}_3$

By using $\{NP[(OCH_2CH_2)_2OCH_3][NHCH(CH_2COOC_2H_5)COOC_2H_5]\}_3$(0.73 g, 0.69 mmol), Ba(OH)$_2 \cdot$8H$_2$O(0.87 g, 2.76 mmol), cyclotriphosphazene-barium salt (0.69 g, 0.61 mmol), and (dach)PtSO$_4$ (0.63 g, 1.83 mmol), the final conjugate product, $\{NP[(OCH_2CH_2)_2OCH_3][L\text{-}Asp.Pt(dach)]\}_3$ (1.05 g, yield, 95.5%) was obtained by the same method as in Example 1.

Molecular formula: $C_{45}H_{87}N_{12}O_{21}P_3Pt_3$

Elemental analysis (%): C, 29.01; H, 4.79; N, 9.39; P, 5.01; Pt, 30.95

Theoretical value: C, 29.85; H, 4.84; N, 9.28; P, 5.13; Pt, 32.33

Proton nuclear magnetic resonance spectrum (D₂O, ppm):

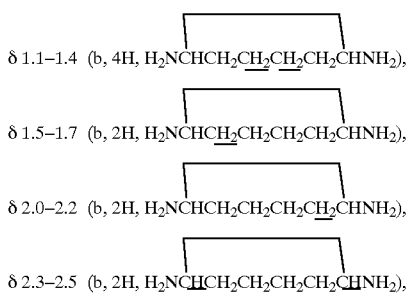

Phosphorus nuclear magnetic resonance spectrum (D₂O, ppm): δ34–44

Lower critical solution temperatures: 92.0° C.

Example 3

Preparation of {NP[(OCH₂CH₂)₂OCH₃][L-Asp.Pt(dmach)]}₃

By using {NP[(OCH₂CH₂)₂OCH₃][NHCH(CH₂COOC₂H₅)COOC₂H₅]}₃ (0.82 g, 0.78 mmol), Ba(OH)₂.8H₂O(0.87 g, 2.76 mmol), cyclotriphosphazene-barium salt (0.74 g, 0.65 mmol),and (dmach)PtSO₄ (0.72 g, 1.96 mmol), the final conjugate product, {NP[(OCH₂CH₂)₂OCH₃][L-Asp.Pt(dmach)]}₃ (0.97 g, yield, 78.2%) was obtained by the same method as in Example 1.

Molecular formula: $C_{51}H_{99}N_{12}O_{21}P_3Pt_3$

Elemental analysis (%): C, 30.22 ; H, 5.15; N, 8.80; P, 4.82; Pt, 29.05

Theoretical value: C, 32.33 ; H, 5.27; N, 8.87; P, 4.90; Pt, 30.89

Proton nuclear magnetic resonance spectrum (D₂O, ppm):
δ1.3–1.6 (b, 10H, H₂NCH₂C(C₅H₁₀)CH₂NH₂),
δ2.4–2.8 (b, 6H, H₂NCH₂C(C₅H₁₀)CH₂NH₂, —NHCH(CH₂COO)COO),
δ3.4 (s, 3H, —O(CH₂CH₂O)₂CH₃),
δ3.6–3.8 (b, 6H, —OCH₂CH₂OCH₂CH₂OCH₃),
δ4.1–4.4 (b, 3H, —OCH₂CH₂OCH₂CH₂OCH₃, —NHCH(CH₂COO)COO), Phosphorus nuclear magnetic resonance spectrum (D₂O, ppm) : δ34–44

Lower critical solution temperatures: 74.5° C.

Example 4

Preparation of {NP[(OCH₂CH₂)₂OCH₃][L-Glu.Pt(dach)]}₃

By using {NP[(OCH₂CH₂)₂OCH₃][NHCH((CH₂)₂COOC₂H₅)COOC₂H₅]}₃ (0.73 g, 0.69 mmol), Ba(OH)₂.8H₂O(0.87 g, 2.76 mmol), cyclotriphosphazene-barium salt (0.69 g, 0.61 mmol), and (dach)PtSO₄ (0.63 g, 1.83 mmol), the final conjugate product, {NP[(OCH₂CH₂)₂OCH₃][L-Glu.Pt(dach)]}₃ (1.05 g, yield, 95.5%) was obtained by the same method as in Example 1.

Molecular formula: $C_{48}H_{93}N_{12}O_{21}P_3Pt_3$

Elemental analysis (%): C, 29.01; H, 4.79; N, 9.39; P, 5.01; Pt, 30.95

Theoretical value: C, 29.85; H. 4.84; N, 9.28; P, 5.13; Pt, 32.33

Proton nuclear magnetic resonance spectrum (D₂O, ppm):

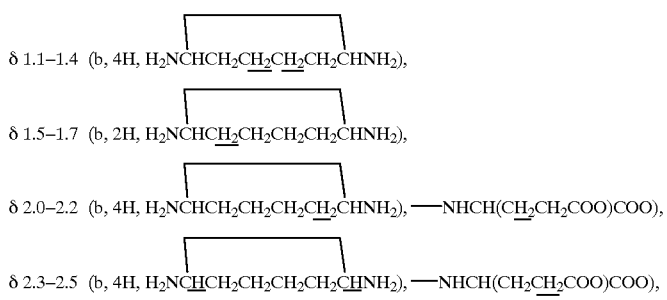

δ3.4 (s, 3H, —O(CH₂CH₂O)₂CH₃),
δ3.6–3.8 (b, 6H, —OCH₂CH₂OCH₂CH₂OCH₃),
δ4.1–4.4 (b, 3H, —OCH₂CH₂OCH₂CH₂OCH₃, —NHCH(CH₂CH₂COO)COO),

Phosphorus nuclear magnetic resonance spectrum (D₂O, ppm): δ34–44

Lower critical solution temperatures: 82.0° C.

Example 5

Preparation of {NP[(OCH₂CH₂)₂OC₂H₅][L-Mal.Pt(dach)]}₃

{NP[(OCH₂CH₂)₂OC₂H₅][NHCH(COOC₂H₅)COOC₂H₅]}₃ (0.50 g, 0.46 mmol), Ba(OH)₂.8H₂O(0.58 g, 1.84 mmol), cyclotriphosphazene-barium salt (0.41 g, 0.35 mmol), and (dach)PtSO₄(0.36 g, 1.56 mmol), the final conjugate product, {NP[(OCH₂CH₂)₂OC₂H₅][L-Mal.Pt(dach)]}₃ (0.46 g, yield, 73.0%) was obtained by the same method as in Example 1.

Molecular formula: $C_{45}H_{87}N_{12}O_{21}P_3Pt_3$

Elemental analysis (%): C, 27.91; H, 4.70; N, 9.17; P, 5.05; Pt, 30.01

Theoretical value: C, 29.86; H, 4.84; N, 9.28; P, 5.13; Pt, 32.33

Proton nuclear magnetic resonance spectrum (D₂O, ppm):

δ 1.1–1.4 (b, 7H, H$_2$NCHCH$_2$C$\underline{H}_2$C$\underline{H}_2$CH$_2$CHNH$_2$), —O(CH$_2$CH$_2$O)$_2$CH$_2$C$\underline{H}_3$), δ 1.5–1.7 (b, 2H, H$_2$NCHC$\underline{H}_2$CH$_2$CH$_2$CH$_2$CHNH$_2$), δ 2.0–2.2 (b, 2H, H$_2$NCHCH$_2$CH$_2$CH$_2$C$\underline{H}_2$CHNH$_2$), δ 2.3–2.5 (b, 2H, H$_2$NC$\underline{H}$CH$_2$CH$_2$CH$_2$CH$_2$C$\underline{H}$NH$_2$), δ3.6–3.8 (b, 8H, —OCH$_2$C$\underline{H}_2$OC$\underline{H}_2$CH$_2$OC$\underline{H}_2$CH$_3$), δ4.1–4.4 (b, 3H, —OC$\underline{H}_2$CH$_2$OC$\underline{H}_2$CH$_2$OCH$_3$, —NHC$\underline{H}$(COO)COO), Phosphorus nuclear magnetic resonance spectrum (D$_2$O, ppm): δ36–46

Lower critical solution temperatures: 39.0° C.

Example 6

Preparation of {NP[(OCH$_2$CH$_2$)$_2$OC$_2$H$_5$][L-Asp.Pt(dmpda)]}$_3$

By using {NP[(OCH$_2$CH$_2$)$_2$OC$_2$H$_5$][NHCH(CH$_2$COOC$_2$H$_5$)COOC$_2$H$_5$]}$_3$(0.80 g, 0.73 mmol), Ba(OH)$_2$.8H$_2$O(0.69 g, 2.91 mmol), cyclotriphosphazene-barium salt (0.64 g, 0.54 mmol), and (dmpda)PtSO$_4$ (0.54 g, 1.63 mmol), the final conjugate product, {NP[(OCH$_2$CH$_2$)$_2$OC$_2$H$_5$][L-Asp.Pt(dmpda)]}$_3$ (0.61 g, yield, 64.0%) was obtained by the same method as in Example 1.

Molecular formula: C$_{45}$H$_{93}$N$_{12}$O$_{21}$P$_3$Pt$_3$

Elemental analysis (%): C, 31.59; H, 5.01 ; N, 9.20; P, 5.20; Pt, 29.98

Theoretical value: C, 29.76 ; H, 5.16; N, 9.25; P, 5.11; Pt, 32.22

Proton nuclear magnetic resonance spectrum (D$_2$O, ppm):

δ0.9–1.1 (b, 6H, H$_2$NCH$_2$C(C$\underline{H}_3$)$_2$C$\underline{H}_2$NH$_2$), δ1.1–1.4 (b, 3H, —O(CH$_2$CH$_2$O)$_2$C$\underline{H}_3$), δ2.2–2.6 (b, 6H, H$_2$NC$\underline{H}_2$C(CH$_3$)$_2$C$\underline{H}_2$NH$_2$, —NHCH(C$\underline{H}_2$COO)COO), δ3.5–3.9 (b, 8H, —OCH$_2$C$\underline{H}_2$OC$\underline{H}_2$CH$_2$OC$\underline{H}_2$CH$_3$), δ4.0–4.3 (b, 3H, —OC$\underline{H}_2$CH$_2$OC$\underline{H}_2$CH$_2$OCH$_3$, —NHC$\underline{H}$(CH$_2$COO)COO), Phosphorus nuclear magnetic resonance spectrum (D$_2$O, ppm): δ34–46

Lower critical solution temperatures: 46.5° C.

Example 7

Preparation of {NP[(OCH$_2$CH$_2$)$_2$OC$_2$H$_5$][L-Asp.Pt(dach)]}$_3$

By using {NP[(OCH$_2$CH$_2$)$_2$OC$_2$H$_5$][NHCH(CH$_2$COOC$_2$H$_5$)COOC$_2$H$_5$]}$_3$ (1.00 g, 0.91 mmol), Ba(OH)$_2$.8H$_2$O(1.15 g, 3.64 mmol), cyclotriphosphazene-barium salt (0.97 g, 0.82 mmol), and (dach)PtSO$_4$ (0.85 g, 2.47 mmol), the final conjugate product, {NP[(OCH$_2$CH$_2$)$_2$OC$_2$H$_5$][L-Asp.Pt(dach)]}$_3$ (1.25 g, yield, 82.2%) was obtained by the same method as in Example 1.

Molecular formula: C$_{48}$H$_{93}$N$_{12}$O$_{21}$P$_3$Pt$_3$

Elemental analysis (%): C, 33.25; H, 4.95; N, 9.15; P, 4.93; Pt, 29.09

Theoretical value: C, 31.12 ; H, 5.06; N, 9.07; P, 5.02 ; Pt, 31.59

Proton nuclear magnetic resonance spectrum (D$_2$O, ppm):

δ 1.1–1.4 (b, 7H, H$_2$NCHCH$_2$C$\underline{H}_2$C$\underline{H}_2$CH$_2$CHNH$_2$), —O(CH$_2$CH$_2$O)$_2$CH$_2$C$\underline{H}_3$), δ 1.5–1.7 (b, 2H, H$_2$NCHC$\underline{H}_2$CH$_2$CH$_2$CH$_2$CHNH$_2$), δ 2.0–2.2 (b, 2H, H$_2$NCHCH$_2$CH$_2$CH$_2$C$\underline{H}_2$CHNH$_2$), δ 2.3–2.5 (b, 2H, H$_2$NC$\underline{H}$CH$_2$CH$_2$CH$_2$CH$_2$C$\underline{H}$NH$_2$), δ2.6–2.9 (b, 2H, —NHCH(C$\underline{H}_2$COO)COO), δ3.6–3.9 (b, 8H, —OCH$_2$C$\underline{H}_2$OC$\underline{H}_2$CH$_2$OC$\underline{H}_2$CH$_3$), δ4.0–4.2 (b, 3H, —OC$\underline{H}_2$CH$_2$OC$\underline{H}_2$CH$_2$OCH$_3$, —NHC$\underline{H}$(CH$_2$COO)COO), Phosphorus nuclear magnetic resonance spectrum(D$_2$O): δ36–44

Lower critical solution temperatures: 42.0° C.

Example 8

Preparation of {NP[(OCH$_2$CH$_2$)$_2$OC$_2$H$_5$][L-Asp.Pt(dmach)]}$_3$

By using {NP[(OCH$_2$CH$_2$)$_2$OC$_2$H$_5$][NHCH(CH$_2$COOC$_2$H$_5$)COOC$_2$H$_5$]}$_3$ (0.65) g, 0.59 mmol), Ba(OH)$_2$8H$_2$O(0.75 g, 2.37 mmol), cyclotriphosphazene-barium salt (0.59 g, 0.50 mmol), and (dmach)PtSO$_4$ (0.55 g, 1.50 mmol), the final conjugate product, {NP[(OCH$_2$CH$_2$)$_2$OC$_2$H$_5$][L-Asp.Pt(dmach)]}$_3$ (0.60 g, yield, 62.5%) was obtained by the same method as in Example 1.

Molecular formula: C$_{54}$H$_{105}$N$_{12}$O$_{21}$P$_3$Pt$_3$

Elemental analysis (%): C, 30.01; H, 5.22; N, 8.58; P, 4.69; Pt, 28.99

Theoretical value: C, 33.49; H, 5.47; N, 8.68 ; P, 4.79; Pt, 30.22

Proton nuclear magnetic resonance spectrum ($D_2O$, ppm):

δ1.2–1.3 (b, 3H, —$OCH_2CH_2OCH_2CH_2O_6CH_2C\underline{H}_3$),

δ1.3–1.6 (b, 10H, $H_2NCH_2C(C_5\underline{H}_{10}CH_2NH_2$)

δ2.5–2.9 (b, 6H, $H_2NC\underline{H}_2C(C_5H_{10})C\underline{H}_2NH_2$, —NHCH(C$\underline{H}_2$COO)COO), δ3.6–3.9 (b, 8H, —$OCH_2C\underline{H}_2OCH_2CH_2O_6C\underline{H}_2CH_3$), δ4.0–4.2 (b, 3H, —$OCH_2C\underline{H}_2OCH_2CH_2OCH_2CH_3$, —NHC$\underline{H}$($CH_2$COO)COO), Phosphorus nuclear magnetic resonance spectrum ($D_2O$, ppm): δ36–46

Lower critical solution temperatures: 35.0° C.

Example 9

Preparation of {NP[($OCH_2CH_2$)$_2OC_3H_7$][L-Asp.Pt(dach)]}$_3$

By using {NP[($OCH_2CH_2$)$_2OC_3H_7$][NHCH($CH_2COOC_2H_5$)$COOC_2H_5$]}$_3$ (0.55 g, 0.50 mmol), Ba(OH)$_2$·$8H_2O$(0.63 g, 2.00 mmol), cyclotriphosphazene-barium salt (0.45 g, 0.37 mmol), and (dach)$PtSO_4$(0.38 g, 1.12 mmol), the final conjugate product, {NP[($OCH_2CH_2$)$_2OC_3H_7$][L-Asp.Pt(dach)]}$_3$ (0.36 g, yield, 50.0%) was obtained by the same method as in Example 1.

Molecular formula: $C_{51}H_{99}N_{12}O_{21}P_3Pt_3$

Elemental analysis (%): C, 31.01; H, 5.30; N, 8.89 ; P, 4.85; Pt, 28.91

Theoretical value: C, 33.49; H, 5.47; N, 8.68; P, 4.79; Pt, 30.22

Proton nuclear magnetic resonance spectrum ($D_2O$, ppm):

δ0.9–1.1 (b, 3H, —$O(CH_2CH_2O)_2CH_2CH_2C\underline{H}_3$),

δ1.1–1.5 (b, 6H, $H_2NCHCH_2C\underline{H}_2CH_2CH_2CHNH_2$), —$O(CH_2CH_2O)_2CH_2C\underline{H}_2CH_3$), δ1.5–1.7 (b, 2H, $H_2NCHC\underline{H}_2CH_2CH_2CH_2CHNH_2$), δ2.0–2.2 (b, 2H, $H_2NCHCH_2CH_2CH_2C\underline{H}_2CHNH_2$), δ2.3–2.7 (b, 4H, $H_2NC\underline{H}CH_2CH_2CH_2C\underline{H}NH_2$), —NHCH(C$\underline{H}_2$COO)COO), δ3.3–3.9 (b, 8H, —$OC\underline{H}_2C\underline{H}_2OC\underline{H}_2CH_2OCH_2CH_2CH_3$), δ4.0–4.3 (b, 3H, —$OC\underline{H}_2CH_2OCH_2CH_2OCH_2CH_2CH_3$, —NHC$\underline{H}$($CH_2$COO)$\overline{C}OO$), Phosphorus nuclear magnetic resonance spectrum ($D_2O$, ppm): δ33–46

Lower critical solution temperatures: 22.0° C.

Example 10

Preparation of {NP[($OCH_2CH_2$)$_2OC_4H_9$][L-Asp.Pt(dach)]}$_3$

By using {NP[($OCH_2CH_2$)$_2OC_4H_9$][NHCH($CH_2COOC_2H_5$)$COOC_2H_5$]}$_3$ (0.55 g, 0.50), Ba(OH)$_2$·$8H_2O$(0.63 g, 2.00 mmol), cyclotriphosphazene-barium salt (0.45 g, 0.37 mmol), and (dach)$PtSO_4$ (0.38 g, 1.12 mmol), the final conjugate product, {NP[($OCH_2CH_2$)$_2OC_4H_9$][L-Asp.Pt(dach)]}$_3$ (0.36 g, yield, 50.0%) was obtain by the same method as in Example 1.

Molecular formula: $C_{54}H_{105}N_{12}O_{21}P_3Pt_3$

Elemental analysis (%): C, 31.01; H, 5.30; N, 8.89; P, 4.85; Pt, 28.91

Theoretical value: C, 33.49; H, 5.47; N, 8.68; P, 4.79; Pt, 30.22

Proton nuclear magnetic resonance spectrum ($D_2O$, ppm):

δ0.9–1.1 (b, 3H, —$O(CH_2CH_2O)_2CH_2(CH_2)_2C\underline{H}_3$),

δ1.1–1.5 (b, 8H, $H_2NCHCH_2C\underline{H}_2CH_2CH_2CHNH_2$], —$O(CH_2CH_2O)_2CH_2(C\underline{H}_2)_2CH_3$)

δ1.5–1.7 (b, 2H, $H_2NCHC\underline{H}_2CH_2CH_2CH_2CHNH_2$),

δ2.0–2.2 (b, 2H, $H_2NCHCH_2CH_2CH_2C\underline{H}_2CHNH_2$),

δ 2.3–2.7 (b, 4H, H$_2$NC$\underline{H}$CH$_2$CH$_2$CH$_2$CH$_2$C$\underline{H}$NH$_2$), —NHCH(C$\underline{H_2}$COO)COO), δ 3.3–3.9 (b, 8H, —OCH$_2$C$\underline{H_2}$OC$\underline{H_2}$CH$_2$OC$\underline{H_2}$(CH$_2$)$_2$CH$_3$), δ 4.0–4.3 (b, 3H, —OC$\underline{H_2}$CH$_2$OCH$_2$CH$_2$O(CH$_2$)$_3$CH$_3$, —NHCH(CH$_2$COO)C$\overline{OO}$), Phosphorus nuclear magnetic resonance spectrum (D$_2$O, ppm): δ33–46

Lower critical solution temperatures: 12.0° C.

Example 11

Preparation of {NP[(OCH$_2$CH$_2$)$_7$OCH$_3$][L-Asp.Pt(dach)]}$_3$

By using {NP[(OCH$_2$CH$_2$)$_7$OCH$_3$][NHCH(CH$_2$COOC$_2$H$_5$)COOC$_2$H$_5$]}$_3$ (0.72 g, 0.42 mmol), Ba(OH)$_2$·8H$_2$O (0.52 g, 1.66 mmol), cyclotriphosphazene-barium salt (0.55 g, 0.28 mmol), and (dach)PtSO$_4$ (0.28 g, 0.83 mmol), the final conjugate product, {NP[(OCH$_2$CH$_2$)$_7$OCH$_3$][L-Asp.Pt(dach)]}$_3$ (0.60 g, yield, 85.7%) was obtained by the same method as in Example 1.

Molecular formula: C$_{75}$H$_{147}$N$_{12}$O$_{36}$P$_3$Pt$_3$

Elemental analysis (%): C, 33.45; H, 5.75; N, 6.68; P, 3.65; Pt, 21.25

Theoretical value: C, 36.03; H, 5.93; N, 6.72; P, 3.72; Pt, 23.41

Proton nuclear magnetic resonance spectrum (D$_2$O, ppm):

δ 1.1–1.5 (b, 4H, H$_2$NCHCH$_2$C$\underline{H_2}$CH$_2$CH$_2$CHNH$_2$)

δ 1.5–1.7 (b, 2H, H$_2$NCHC$\underline{H_2}$CH$_2$CH$_2$CH$_2$CHNH$_2$),

δ 2.0–2.2 (b, 2H, H$_2$NCHCH$_2$CH$_2$CH$_2$C$\underline{H_2}$CHNH$_2$),

δ 2.3–2.5 (b, 2H, H$_2$NC$\underline{H}$CH$_2$CH$_2$CH$_2$CH$_2$C$\underline{H}$NH$_2$), δ 2.6–2.9 (b, 2H, —NHCH(C$\underline{H_2}$COO)COO), δ 3.3–3.4 (s, 3H, —O(CH$_2$CH$_2$O)$_7$C$\underline{H_3}$), δ 3.6–3.9 (b, 26H, —OCH$_2$CH$_2$O(C$\underline{H_2}$CH$_2$O)$_6$CH$_3$), Phosphorus nuclear magnetic resonance spectrum (D$_2$O, ppm): δ38–42

Lower critical solution temperatures: 84.0° C.

Example 12

Preparation of {NP[(OCH$_2$CH$_2$)$_{12}$OCH$_3$][L-Asp.Pt(dach)]}$_3$

By using {NP[(OCH$_2$CH$_2$)$_{12}$OCH$_3$][NHCH(CH$_2$COOC$_2$H$_5$)COOC$_2$H$_5$]}$_3$ (0.67 g, 0.29 mmol), Ba(OH)$_2$·8H$_2$O(0.36 g, 1.14 mmol), cyclotriphosphazene-barium salt (0.68 g, 0.26 mmol), and (dach)PtSO$_4$ (0.27 g, 0.79 mmol), the final conjugate product, {NP[(OCH$_2$CH$_2$)$_{12}$OCH$_3$][L-Asp.Pt(dach)]}$_3$ (0.66 g, yield, 81.5%) was obtained by the same method as in Example 1.

Molecular formula: C$_{105}$H$_{207}$N$_{12}$O$_{51}$P$_3$Pt$_3$

Elemental analysis (%): C, 38.75; H, 6.85; N, 5.35; P, 2.89; Pt, 19.05

Theoretical value: C, 40.68; H, 6.73; N, 5.42; P, 2.99; Pt, 18.88

Proton nuclear magnetic resonance spectrum (D$_2$O, ppm):

δ 1.1–1.5 (b, 4H, H$_2$NCHCH$_2$C$\underline{H_2}$CH$_2$CH$_2$CHNH$_2$)

δ 1.5–1.7 (b, 2H, H$_2$NCHC$\underline{H_2}$CH$_2$CH$_2$CH$_2$CHNH$_2$),

δ 2.0–2.2 (b, 2H, H$_2$NCHCH$_2$CH$_2$CH$_2$C$\underline{H_2}$CHNH$_2$),

δ 2.3–2.5 (b, 2H, H$_2$NC$\underline{H}$CH$_2$CH$_2$CH$_2$CH$_2$C$\underline{H}$NH$_2$), δ 2.6–2.9 (b, 2H, —NHCH(C$\underline{H_2}$COO)COO), δ 3.3–3.4 (s, 3H, —O(CH$_2$CH$_2$O)$_{12}$C$\underline{H_3}$), δ 3.6–3.9 (b, 26H, —OCH$_2$CH$_2$O(C$\underline{H_2}$CH$_2$O)$_{11}$CH$_3$), δ 4.0–4.2 (b, 3H, —OC$\underline{H_2}$CH$_2$O(C$\underline{H_2}$CH$_2$O)$_{11}$CH$_3$, —NHC$\underline{H}$(CHCOO)COO), Phosphorus nuclear magnetic resonance spectrum (D$_2$O, ppm): δ34–46

Lower critical solution temperatures: not observed (above 100° C.)

Bioassay on the Cyclotriphosphazene-Pt Conjugates of the Present Invention

The antitcancer activity of the complexes prepared according to the Examples of the present invention was assayed as follows.

1. Determination of in vitro activity
   (1) Samples: Example 2, Example 6, Example 7 and Example 11
   (2) Cancer cell line: mouse leukemia L1210 cell line
   (3) Experimental method: The L1210 cells were cultured in RPMI 1640 medium supplemented with 10% FBS, and the concentration of the cells were controlled to 1×10$^5$ cells/ml. After adding the samples each serially diluted by logarithmic dose to the cells, cells were cultured in an incubator at 37° C. and under 5% CO$_2$ atmosphere.

The viable cell number was determined after 24, 48 and 72 hours by using trypan blue dye exclusion test. By comparing with the cell numbers of the control group (where no chemical treatment was performed), the concentration of each compound exhibiting 50% of cell growth inhibition (ED$_{50}$) was calculated. The results are shown in Table 1.

2. Determination of in vivo (i.p.) activity
   (1) Samples: Example 2, Example 6, Example 7 and Example 11
   (2) Cancer cell line: mouse leukemia L1210 cell line
   (3) Experimental method: The leukemia L1210 cells(1× 10$^5$ cells/0.1 ml) obtained from DBA/2 donor mice were injected intraperitoneally to the BDF1 mice (6–8 weeks old, 8 mice per group). The samples were either dissolved in PBS solution or suspended in 0.5% Tween 80 depending on their solubility. These sample solutions were administered via intraperitoneal injection once a day for 5 consecutive days or at day 1, 5, and 9 after the cancer cell implantation at variable dosages. The survival rate was determined by observing the mice each day. By comparing with the average survival time of the control group (where no chemical treatment was performed), the percent average increase in the survival time(T/C, %) was calculated to determine the anticancer activity. The results are shown in Table 1.

TABLE 1

Results of bioassay on the cyclotriphosphazene-Pt conjugates

| Compound | In vitro ED$_{50}$ ($\mu$M) | In vivo (i.p.) Dose (mgkg$^{-1}$) | T/C (%) |
|---|---|---|---|
| Example 2 | 0.4 | 90 | >511.0 |
|  |  | 60 | >293.8 |
|  |  | 30 | 217.3 |
| Example 6 |  | 60 | 162.0 |
|  |  | 30 | 146.1 |
| Example 7 | 0.4 | 80 | >271.7 |
|  |  | 60 | 226.7 |
|  |  | 40 | 200.8 |
| Example 11 | 0.2 | 90 | 204.2 |
|  |  | 60 | 229.2 |
|  |  | 30 | 197.0 |
| Cisplatin | 0.7 | 4 | 163.0 |
| Carboplatin | 5.9 | 40 | 168.0 |

EFFECT OF INVENTION

According to the present invention, a novel class of cyclotriphosphazene platinum conjugate anticancer agents were provided, which have a stereo-specific chemical structure and thermosensitivity. The cyclotriphosphazene-platinum conjugates according to the present invention exhibit thermosensitivity whose transition temperature can be designed variably for the desired purpose and controlled precisely. The thermosensitive cyclotriphosphazene-platinum conjugate anticancer agent according to the invention can be applied in the treatment of cancers via either systemic or local administration.

What is claimed is:

1. A cyclotriphosphazene-platinum complex conjugate represented by Formula 1

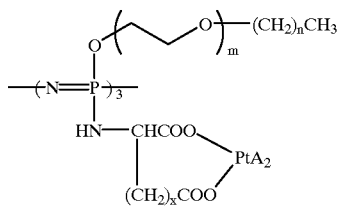

Formula 1 wherein, m is an integer selected from 2, 7 and 12; n is an integer selected from 0, 1, 2 and 3; x is an integer selected from 0, 1 and 2; and A$_2$ is a bidentate chelating diamine selected from the group consisting of 2,2-dimethyl-1,3-propanediamine, trans($\pm$)-1,2-diaminocyclohexane and 1,1-diaminomethylcyclohexane.

2. The compound according to claim 1 which has thermosensitivity.

3. A method of preparing a cyclotriphosphazene-platinum complex conjugate represented by Formula 1 according to claim 1 comprising the following steps;

(1) hydrolysis process of the trimeric amino acid ester derivatives of Formula 2 with alkali earth metal hydroxide of Formula 3 or alkali metal hydroxide of Formula 4 to obtain the intermediate cyclotriphosphazene-alkali earth metal salt of Formula 5 or cyclotriphosphazene-alkali metal salt of Formula 6, respectively;

(2) reacting the intermediate cyclotriphosphazene-metal salt of Formulas 5 or 6 with (diamine)platinum (II) salt of Formula 7 in a mole ratio of 1:3 to obtain the cyclotriphosphazene-platinum complex conjugates of Formula 1 according to the claim 1

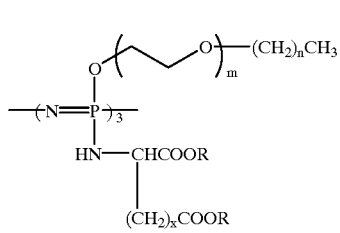

Formula 2

M(OH)$_2$    Formula 3

M'OH    Formula 4

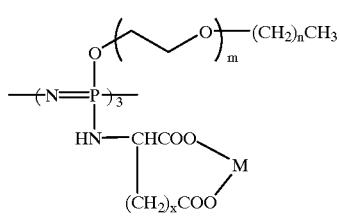

Formula 5

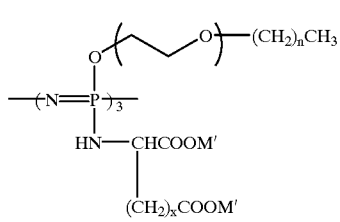

Formula 6

A$_2$PtL2    Formula 7 wherein, m is an integer selected from 2, 7 and 12; n is an integer selected from 0, 1, 2 and 3; x is an integer selected from 0, 1 and 2; A$_2$ is a bidentate chelating diamine selected from the group consisting of 2,2-dimethyl-1,3-propanediamine, trans($\pm$)-1,2-diaminocyclohexane and 1,1-diaminomethyl-cyclohexane; R is selected from the group consisting of methyl, ethyl and benzyl groups; M is an alkali earth metal ions; M' is an alkali metal ions; and L$_2$ is sulfate or nitrate anion.

4. The method according to claim 3, wherein the alkali earth metal of Formula 3 is barium or calcium, the alkali metal of Formula 4 is lithium, sodium or potassium, and the platinum salt of Formula 7 is (diamine)platinum(II) sulfate or (diamine)platinum(II) nitrate.

5. The method according to claim 3, wherein the insoluble byproduct barium sulfate, produced by the reaction of cyclotriphosphazene-barium salt of Formula 5 with (diamine)platinum(II) sulfate of Formula 7 in an aqueous solution, is removed by centrifugation or filtration.

6. The method according to claim 4, wherein the insoluble byproduct barium sulfate, produced by the reaction of cyclotriphosphazene-barium salt of Formula 5 with (diamine)platinum(II) sulfate of Formula 7 in an aqueous solution, is removed by centrifugation or filtration.

7. The method according to claim 3, wherein the byproduct sodium sulfate, produced by the reaction of cyclotriphosphazene-sodium salt of Formula 6 with (diamine)platinum(II) sulfate of Formula 7 in an aqueous solution, is removed by dialysis.

8. The method according to claim 4, wherein the byproduct sodium sulfate, produced by the reaction of cyclotriphosphazene-sodium salt of Formula 6 with (diamine)platinum(II) sulfate of Formula 7 in an aqueous solution, is removed by dialysis.

9. The method according to claim 3, wherein the intermediate cyclotriphosphazene-metal salt of Formula 5 or 6 produced by hydrolyzing cyclotriphosphazene derivatives of Formula 2 with an alkali earth metal hydroxide of Formula 3 or an alkali metal hydroxide of Formula 4, respectively in methanol, is precipitated by the addition of an excess amount of ethyl ether or hexane.

10. The method according to claim 4, wherein the intermediate cyclotriphosphazene-metal salt of Formula 5 or 6 produced by hydrolyzing cyclotriphosphazene derivatives of Formula 2 with an alkali earth metal hydroxide of Formula 3 or an alkali metal hydroxide of Formula 4, respectively in methanol, is precipitated by the addition of an excess amount of ethyl ether or hexane.

11. The method according to claim 3, wherein the cyclotriphosphazene-platinum complex conjugate of Formula 1 is extracted by using methanol or ethanol as solvent after reacting the cyclotriphosphazene-metal salt of Formula 5 or 6 with (diamine)platinum(II) sulfate of Formula 7 at 1~5° C. for 5~10 hour in an aqueous solution and freeze drying.

12. The method according to claim 4, wherein the cyclotriphosphazene-platinum complex conjugate of Formula 1 is extracted by using methanol or ethanol as solvent after reacting the cyclotriphosphazene-metal salt of Formula 5 or 6 with (diamine)platinum(II) sulfate of Formula 7 at 1~5° C for 5~10 hour in an aqueous solution and freeze drying.

13. The method of obtaining the pure final product of Formula 1 through precipitation process by adding an excess amount of ether or hexane to the methanol or ethanol solution of the product obtained in claim 8.

14. The anticancer composition comprising cyclotriphosphazene-platinum complex conjugate of claim 1 as an active ingredient.

15. The anticancer composition comprising cyclotriphosphazene-platinum complex conjugate of claim 2 as an active ingredient.

* * * * *

UNITED STATES PATENT AND TRADEMARK OFFICE
CERTIFICATE OF CORRECTION

PATENT NO.     : 6,333,422 B1
DATED          : December 25, 2001
INVENTOR(S)    : Youn Soo Sohn et al.

It is certified that error appears in the above-identified patent and that said Letters Patent is hereby corrected as shown below:

<u>Title page,</u>
Item [30], Foreign Application Priority Data,
Change the priority number from "12-48360" to -- 00-48360 --.

Signed and Sealed this

Fifteenth Day of July, 2003

JAMES E. ROGAN
*Director of the United States Patent and Trademark Office*